(12) United States Patent
Satterfield

(10) Patent No.: US 8,673,569 B2
(45) Date of Patent: Mar. 18, 2014

(54) PRIMERS FOR NUCLEIC ACID EXTENSION OR AMPLIFICATION REACTIONS

(75) Inventor: Brent C. Satterfield, Greenwood, SC (US)

(73) Assignee: DNA Logix, Inc., Bountiful, UT (US)

(*) Notice: Subject to any disclaimer, the term of this patent is extended or adjusted under 35 U.S.C. 154(b) by 593 days.

(21) Appl. No.: 12/830,242

(22) Filed: Jul. 2, 2010

(65) Prior Publication Data

US 2011/0027786 A1  Feb. 3, 2011

Related U.S. Application Data

(60) Provisional application No. 61/222,908, filed on Jul. 2, 2009.

(51) Int. Cl.
*C12Q 1/68* (2006.01)
*C12P 19/34* (2006.01)

(52) U.S. Cl.
USPC .......................................... 435/6.12; 435/91.2

(58) Field of Classification Search
None
See application file for complete search history.

(56) References Cited

U.S. PATENT DOCUMENTS 7,041,255 B2 * 5/2006 Wang ............................ 422/430

OTHER PUBLICATIONS

Deubel et al. (GenBank No. M20558.1, Dengue virus type 2 Jamaica/N. 1409, complete genome (2002).*

* cited by examiner

*Primary Examiner* — Kenneth R. Horlick
*Assistant Examiner* — David Thomas
(74) *Attorney, Agent, or Firm* — Meunier Carlin & Curfman, LLC

(57) ABSTRACT

Disclosed are methods and compositions for use in nucleic acid amplification or extension reactions.

6 Claims, 3 Drawing Sheets

Figure 2.

| NAME | SEQUENCE | TARGET SEQUENCE |
|---|---|---|
| F1 | GGAAGCTGTACGC GACTAGTGGTTAGAGGAGA (SEQ ID NO:1) | CcatgcgCcac<u>GGAAGCTGTA</u>cgcgtgGcaTAttg<br><u>GACTAGtGGTTAGAGGAGA</u>CCCCTCCCatta<br>tcaAcaaaacGCAgcAcaaaaggGGgcCCgAagtcaggatg<br>AAGCTGTActcctgatggAAGGACtAGcGGTTAgaG<br>GAGACCCCCcccaacacaaaAAcaCAGCATATTGAC<br>gCTGGGAaAGACCAGAGATCCTGCTGTCTCtgC<br>AaCATCAaTCCAGGCACAGAgCGCC |
| F2 | GGAAGCTGTACGC GACTAGTGGTTAGAGGA (SEQ ID NO:2) | CcatgcgCcac<u>GGAAGCTGTA</u>cgcgtgGcaTAttg<br><u>GACTAGtGGTTAGAGGA</u>GACCCCTCCCatta<br>tcaAcaaaacGCAgcAcaaaaggGGgcCCgAagtcaggatg<br>AAGCTGTActcctgatggAAGGACtAGcGGTTAgaG<br>GAGACCCCCcccaacacaaaAAcaCAGCATATTGAC<br>gCTGGGAaAGACCAGAGATCCTGCTGTCTCtgC<br>AaCATCAaTCCAGGCACAGAgCGCC |
| F3 | GGAAGCTGTA ACTAGTGGTTAGAGGA (SEQ ID NO:3) | CcatgcgCcac<u>GGAAGCTGTA</u>cgcgtgGcaTAttg<br><u>GACTAGtGGTTAGAGGA</u>GACCCCTCCCatta<br>tcaAcaaaacGCAgcAcaaaaggGGgcCCgAagtcaggatg<br>AAGCTGTActcctgatggAAGGACtAGcGGTTAgaG<br>GAGACCCCCcccaacacaaaAAcaCAGCATATTGAC<br>gCTGGGAaAGACCAGAGATCCTGCTGTCTCtgC<br>AaCATCAaTCCAGGCACAGAgCGCC |
| R1 | CTGTGCCTGGA GAGACAGCAGGA (SEQ ID NO:4) | CcatgcgCcacGGAAGCTGTAcgcgtgGcaTAttg<br>GACTAGtGGTTAGAGGAGACCCCTCCCatta<br>tcaAcaaaacGCAgcAcaaaaggGGgcCCgAagtcaggatg<br>AAGCTGTActcctgatggAAGGACtAGcGGTTAgaG<br>GAGACCCCCcccaacacaaaAAcaCAGCATATTGAC<br>gCTGGGAaAGACCAGAGA<u>TCCTGCTGTCTC</u>tgC<br>AaCATCAa<u>TCCAGGCACAGA</u>gCGCC |
| R2 | CTGTGCCTGGA GAGACAGCAGGAT (SEQ ID NO:5) | CcatgcgCcacGGAAGCTGTAcgcgtgGcaTAttg<br>GACTAGtGGTTAGAGGAGACCCCTCCCatta<br>tcaAcaaaacGCAgcAcaaaaggGGgcCCgAagtcaggatg<br>AAGCTGTActcctgatggAAGGACtAGcGGTTAgaG<br>GAGACCCCCcccaacacaaaAAcaCAGCATATTGAC<br>gCTGGGAaAGACCAGAG<u>ATCCTGCTGTCTC</u>tgC<br>AaCATCAa<u>TCCAGGCACAGA</u>gCGCC |
| R3 | CTGTGCCTGGA GAGACAGCAGGATCT (SEQ ID NO:6) | CcatgcgCcacGGAAGCTGTAcgcgtgGcaTAttg<br>GACTAGtGGTTAGAGGAGACCCCTCCCatta<br>tcaAcaaaacGCAgcAcaaaaggGGgcCCgAagtcaggatg<br>AAGCTGTActcctgatggAAGGACtAGcGGTTAgaG<br>GAGACCCCCcccaacacaaaAAcaCAGCATATTGAC<br>gCTGGGAaAGACCAG<u>AGATCCTGCTGTCTC</u>tgC<br>AaCATCAa<u>TCCAGGCACAGA</u>gCGCC |

```
SEQUENCE LISTING

<160> NUMBER OF SEQ ID NOS: 6

<210> SEQ ID NO 1
<211> LENGTH: 32
<212> TYPE: DNA
<213> ORGANISM: Dengue virus

<400> SEQUENCE: 1
ggaagctgta cgcgactagt ggttagagga ga                                 32

<210> SEQ ID NO 2
<211> LENGTH: 30
<212> TYPE: DNA
<213> ORGANISM: Dengue virus

<400> SEQUENCE: 2
ggaagctgta cgcgactagt ggttagagga                                    30

<210> SEQ ID NO 3
<211> LENGTH: 26
<212> TYPE: DNA
<213> ORGANISM: Dengue virus

<400> SEQUENCE: 3
ggaagctgta actagtggtt agagga                                        26

<210> SEQ ID NO 4
<211> LENGTH: 23
<212> TYPE: DNA
<213> ORGANISM: Dengue virus

<400> SEQUENCE: 4
ctgtgcctgg agagacagca gga                                           23

<210> SEQ ID NO 5
<211> LENGTH: 24
<212> TYPE: DNA
<213> ORGANISM: Dengue virus

<400> SEQUENCE: 5
ctgtgcctgg agagacagca ggat                                          24

<210> SEQ ID NO 6
<211> LENGTH: 26
<212> TYPE: DNA
<213> ORGANISM: Dengue virus

<400> SEQUENCE: 6
ctgtgcctgg agagacagca ggatct                                        26
```

PRIMERS FOR NUCLEIC ACID EXTENSION OR AMPLIFICATION REACTIONS

CROSS-REFERENCE TO RELATED APPLICATIONS

This application claims priority to U.S. Provisional Application No. 61/222,908, entitled PRIMERS FOR NUCLEIC ACID EXTENSION OR AMPLIFICATION REACTIONS, which was filed on Jul. 2, 2009, the disclosure of which is hereby incorporated by reference in its entirety.

The present application is being filed along with a Sequence Listing in electronic format. The Sequence Listing is provided as a file entitled CDIAG_005A.TXT, created on Jun. 30, 2010, which is 1 Kb in size. The information in the electronic format of the Sequence Listing is incorporated herein by reference in its entirety.

BACKGROUND

1. Field

The present technology is related to methods and compositions for nucleic acid extension or amplification reactions.

2. Description of the Related Art

Numerous methods of amplification of a nucleic acid are known to those skilled in the art. In general, the amplification of a nucleic acid sequence includes creating one or more copies of the nucleic acid sequence or of a secondary nucleic acid sequence that may be indicative of the presence of the first nucleic acid. Examples include, but are not limited to, polymerase chain reaction (PCR), rolling circle amplification (RCA), nucleic acid sequence based amplification (NASBA), transcription-mediated amplification (TMA), ligase chain reaction (LCR), and loop-mediated isothermal amplification (LAMP), among others. In some technologies, a nucleic acid sequence indicative of the presence of a non-nucleic acid structure (e.g., a protein) is amplified, as in the proximity ligation assay (PLA) and other amplification methods. Methods of extension of a nucleic acid are also known to those skilled in the art.

The majority of these methods require a short nucleic acid sequence to "prime" the amplification reaction by providing a 3' hydroxyl group upon which the target amplicon may be built. This nucleic acid sequence used to prime the reaction is referred to as a primer.

SUMMARY

The present technology generally relates to methods and compositions of primers for nucleic acid extension or amplification reactions.

Some embodiments relate to split primers for initiating a nucleic acid amplification or extension reaction. The primers may be, for example, less than 100 bases and may include at least two regions capable of binding to at least two target regions. The at least two target regions may be separated, for example, by at least one nucleic acid base, and the two or more regions of the primer do not need to be separated by at least one nucleic acid base.

The split primer can include, for example, a primer whose two or more regions, capable of binding to at least two target regions, are not separated by an intervening base. The split primer can include a primer whose two or more unique locations on the target nucleic acid are separated by at least three nucleic acid bases. The split primer can include a primer whose two or more unique locations on the target nucleic acid are separated by at least five nucleic acid bases. The split primer can include a primer whose target nucleic acid is derived from the Dengue virus. The split primer can include a primer whose sequence is selected from the group consisting of SEQ ID NO: 1, 2, 3, 4, 5, and 6.

In some aspects, the split primer can include, for example, one or more of the following: (a) a nucleic acid sequence that can be selected from the group consisting of SEQ ID NOs:1, 2, 3, 4, 5, and 6; (b) a nucleic acid sequence that has 80%-99% identity (or any value in between or subrange in between) to a nucleic acid sequence selected from the group consisting of SEQ ID NOs:1, 2, 3, 4, 5, and 6; (c) a nucleic acid sequence that can have 95%-99% identity to a nucleic acid sequence selected from the group consisting of SEQ ID NOs:1, 2, 3, 4, 5, and 6; (d) a nucleic acid sequence that can differ in as many as 6 nucleotide positions from a nucleic acid sequence selected from the group consisting of SEQ ID NOs:1, 2, 3, 4, 5, and 6; (e) a nucleic acid sequence that can differ in as many as 3 nucleotide positions from a nucleic acid sequence selected from the group consisting of SEQ ID NOs:1, 2, 3, 4, 5, and 6; (f) a nucleic acid sequence that can be selected from the group consisting of SEQ ID NOs:1, 2, 3, 4, 5, and 6, wherein the nucleic acid sequence includes between 1-5 nucleotide analog substitutions or non-naturally occurring nucleotide substitutions; or (g) a sequence complementary to any of (a)-(e).

Some embodiments relate to kits including, for example, a split primer as described above and elsewhere herein, and a set of instructions for use as a primer in an amplification or extension reaction. Some embodiments relate to a kit that includes, for example, a primer whose sequence is selected from the group consisting of SEQ ID NO: 1, 2, 3, 4, 5, and 6, a primer with 80% to 99% similarity to these primers and any number in between, a primer that can differ in as many as six nucleotide positions from one of these primers, a primer that can differ in as many as three nucleotide positions from one of these primers, a primer that differs from one of these primers by the inclusion of, for example, 1-5 nucleotide analogue substitutions, or, for example, a primer complementary to one or more of the primers above, and a set of instructions for use, for example, in an amplification or extension reaction.

Some embodiments relate to methods of assaying for a nucleic acid sequence, the methods including, for example, contacting a split primer with a sample that may include DNA derived from a Dengue virus, for example, under conditions necessary for the amplification, wherein the split primer may target two or more unique locations on a target nucleic acid, for example from the Dengue virus, and wherein the two or more unique locations may be separated by at least one nucleic acid base, and wherein amplification or extension of the target sequence may be indicative of the presence of DNA derived from, for example, Dengue virus, in the sample.

Some embodiments relate to methods of assaying for a nucleic acid sequence, wherein the split primer may target two or more unique locations on a target nucleic acid, for example from the Dengue virus, and wherein the two or more unique locations may be separated by at least three nucleic acid bases.

Some embodiments relate to methods of assaying for a nucleic acid sequence, wherein the split primer may target two or more unique locations on a target nucleic acid, for example from the Dengue virus, and wherein the two or more unique locations may be separated by at least five nucleic acid bases.

Some embodiments relate to methods of assaying for a nucleic acid sequence, wherein the split primer may target two or more unique locations on a target nucleic acid, where the method further includes detecting a product from the amplification and/or includes detecting the presence of the target nucleic acid.

Some embodiments relate to methods of amplifying a target nucleic acid sequence. The methods may include, for example, providing a split primer, wherein the split primer includes a first sequence complementary to a first region of a target nucleic acid sequence and a second sequence complementary to a second region of a target nucleic acid, wherein the first and second regions of the target nucleic acid sequence are separated by at least one nucleic acid base. The method may further include, for example, hybridizing the split primer to the first and second regions of the target nucleic acid sequence. The methods may further include, for example, amplifying the target nucleic acid sequence.

Some embodiments relate to methods of generating a primer suitable for use in an amplification or extension reaction. These methods may include, for example, identifying two or more regions of high conservation in a template nucleotide sequence, such that the compliment of the 5'-most of these regions is unique in the template. This method may further include, for example, synthesizing a primer that comprises sequences complimentary to the two or more regions of high conservation, fused to one another with no intervening sequence and in the same relative order but the opposite orientation as the sequences appear in the template.

Some embodiments relate to methods of generating a primer suitable for use in an amplification or extension reaction where the primer is 10 to 100 bases long, for example.

Some embodiments relate to a method of generating a primer suitable for use in an amplification or extension reaction where the primer is 20 to 50 bases long. Some embodiments relate to a method of generating a primer suitable for use in an amplification or extension reaction where the primer includes sequence identical at 80-99% of its nucleotide positions to the complimentary sequence to the two or more regions of high conservation.

Some embodiments relate to methods of generating a primer suitable for use in an amplification or extension reaction where the primer includes, for example, sequence identical at 95-99% of its nucleotide positions to the reverse compliment sequence to the two or more regions of high conservation.

Some embodiments relate to methods of generating a primer suitable for use in an amplification or extension reaction where the primer includes, for example, sequence differing at up to three nucleotide positions from sequence complimentary to the two or more regions of high conservation.

Some embodiments relate to methods of generating a primer suitable for use in an amplification or extension reaction where the primer includes, for example, sequence differing at up to six nucleotide positions from sequence complimentary to the two or more regions of high conservation.

One embodiment relates to split primers for initiating a nucleic acid amplification or extension reaction which binds to, anneals to or otherwise targets two or more unique locations on the target nucleic acid template each separated by at least one nucleic acid base.

Another embodiment relates to split primers for initiating a nucleic acid amplification or extension reaction which targets two or more unique locations on the target nucleic acid each separated by at least three nucleic acid bases.

A further embodiment relates to split primers for initiating a nucleic acid amplification or extension reaction which targets two or more unique locations on the target nucleic acid each separated by at least five nucleic acid bases.

A further embodiment relates to methods for amplifying a nucleic acid sequence, which can include, for example, contacting a primer as described herein with a sample comprising a nucleic acid under conditions necessary for amplification.

A further embodiment relates to methods for extending a nucleic acid sequence off of a primer, comprising contacting a primer as described herein with a sample comprising a nucleic acid under conditions necessary for extension.

A further embodiment relates to methods for detecting a nucleic acid sequence, comprising detecting a product of a method as described herein.

A further embodiment relates to a split primer for use in a nucleic acid amplification or extension reaction, in a sample that may comprise DNA derived from a Dengue virus, where the split primer targets two or more unique locations on a target nucleic acid from the Dengue virus, and where the two or more unique locations are each separated by at least one nucleic acid base. In one embodiment, the two or more unique locations are each separated by at least three nucleic acid bases. In another embodiment, the two or more unique locations are each separated by at least five nucleic acid bases.

A further embodiment relates to split primers for use in a nucleic acid amplification or extension reaction in a sample comprising a Dengue virus, the split primer comprising: (a) a nucleic acid sequence of SEQ ID NO:1; (b) a sequence having 95%-99% identity to SEQ ID NO:1; (c) a nucleic acid sequence of SEQ ID NO:1 with between 1-5 nucleotide analog or non-naturally occurring nucleotide substitutions; or (d) a sequence complementary to any of (a)-(c).

A further embodiment relates to split primers for use in a nucleic acid amplification or extension reaction in a sample comprising a Dengue virus, the split primer comprising: (a) a nucleic acid sequence of SEQ ID NO:1; (b) a sequence having 95%-99% identity to SEQ ID NO:1; (c) a nucleic acid sequence of SEQ ID NO:1 with between 1-5 nucleotide analog or non-naturally occurring nucleotide substitutions; or (d) a sequence complementary to any of (a)-(c).

A further embodiment relates to split primers for use in a nucleic acid amplification or extension reaction in a sample comprising a Dengue virus, the split primer comprising: (a) a nucleic acid sequence of SEQ ID NO:2; (b) a sequence having 95%-99% identity to SEQ ID NO:2; (c) a nucleic acid sequence of SEQ ID NO:2 with between 1-5 nucleotide analog or non-naturally occurring nucleotide substitutions; or (d) a sequence complementary to any of (a)-(c).

A further embodiment relates to split primers for use in a nucleic acid amplification or extension reaction in a sample comprising a Dengue virus, the split primer comprising: (a) a nucleic acid sequence of SEQ ID NO:3; (b) a sequence having 95%-99% identity to SEQ ID NO:3; (c) a nucleic acid sequence of SEQ ID NO:3 with between 1-5 nucleotide analog or non-naturally occurring nucleotide substitutions; or (d) a sequence complementary to any of (a)-(c).

A further embodiment relates to split primers for use in a nucleic acid amplification or extension reaction in a sample comprising a Dengue virus, the split primer comprising: (a) a nucleic acid sequence of SEQ ID NO:4; (b) a sequence having 95%-99% identity to SEQ ID NO:4; (c) a nucleic acid sequence of SEQ ID NO:4 with between 1-5 nucleotide analog or non-naturally occurring nucleotide substitutions; or (d) a sequence complementary to any of (a)-(c).

A further embodiment relates to split primers for use in a nucleic acid amplification or extension reaction in a sample comprising a Dengue virus, the split primer comprising: (a) a nucleic acid sequence of SEQ ID NO:5; (b) a sequence having 95%-99% identity to SEQ ID NO:5; (c) a nucleic acid sequence of SEQ ID NO:5 with between 1-5 nucleotide analog or non-naturally occurring nucleotide substitutions; or (d) a sequence complementary to any of (a)-(c).

A further embodiment relates to split primers for use in a nucleic acid amplification or extension reaction in a sample comprising a Dengue virus, the split primer comprising: (a) a nucleic acid sequence of SEQ ID NO:6; (b) a sequence having 95%-99% identity to SEQ ID NO:6; (c) a nucleic acid sequence of SEQ ID NO:6 with between 1-5 nucleotide analog or non-naturally occurring nucleotide substitutions; or (d) a sequence complementary to any of (a)-(c).

A further embodiment relates to methods for amplifying a nucleic acid sequence, the method comprising contacting a split primer with a sample comprising a Dengue virus under conditions necessary for the amplification, where the split primer targets two or more unique locations on a target nucleic acid from the Dengue virus, and where the two or more unique locations are separated by at least one nucleic acid base. In one embodiment, the two or more unique locations are separated by at least three nucleic acid bases. In another embodiment, the two or more unique locations are separated by at least five nucleic acid bases. In a further embodiment, the method further comprises detecting a product from the amplification.

A further embodiment relates to methods for extending a nucleic acid sequence, the method comprising contacting a split primer with a sample comprising a Dengue virus under conditions necessary for the extension, where the split primer targets two or more unique locations on a target nucleic acid from the Dengue virus, and where the two or more unique locations are separated by at least one nucleic acid base. In one embodiment, the two or more unique locations are separated by at least three nucleic acid bases. In another embodiment, the two or more unique locations are separated by at least five nucleic acid bases. In a further embodiment, the method further comprises detecting a product from the extension.

A further embodiment relates to kits that include, without limitation, a split primer as described herein and a set of instructions for use in an amplification or extension reaction.

Some embodiments relate to methods for designing primers to target highly polymorphic organisms and/or broad classes of organisms. For example, methods may include designing a primer to hybridize with two or more distinct regions on the target nucleic acid. This allows the primer to obtain desired melting temperatures and reaction temperatures, while simultaneously enabling the targeting of preferred sequences, such as those that are conserved and have optimal GC content.

One of skill in the art, with the benefit of this application, will know that the embodiments described herein can be applied to many nucleic acid amplification and extension technologies.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

FIG. 2. Primer Sequences Targeting Dengue virus. Split primer sequences used in the detection of Dengue virus types 1-4 are shown. Mismatches from 74 aligned Dengue viruses are indicated by lower case text. Regions of the target where the primers bind are underlined.

DETAILED DESCRIPTION

Figure 1:
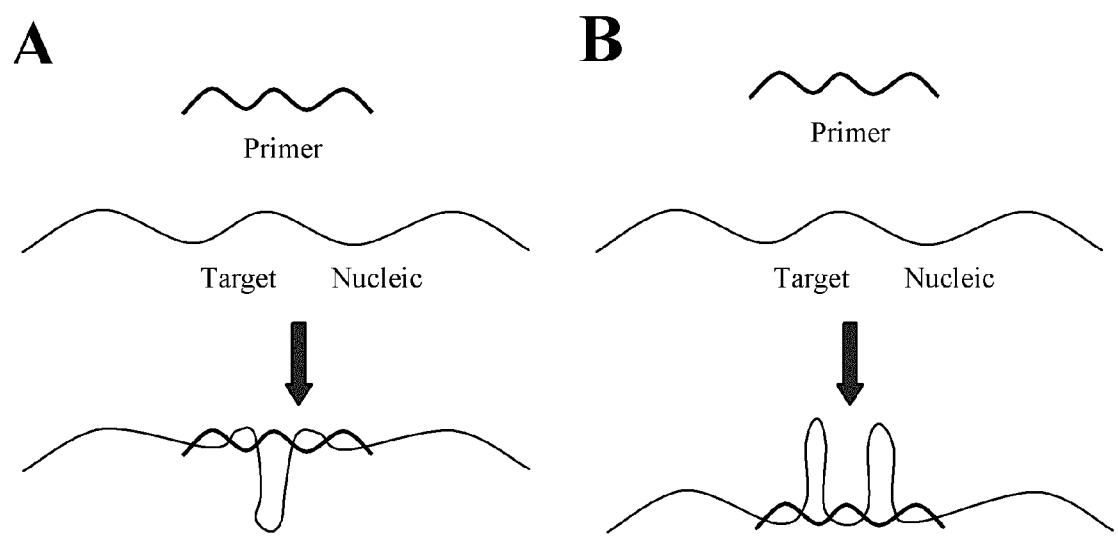
FIG. 1. Primers Targeting Multiple Unique Locations. (A) A primer which hybridizes with two unique locations on a target is shown. (B) A primer which hybridizes with three unique locations on a target is shown.
Figure 3:
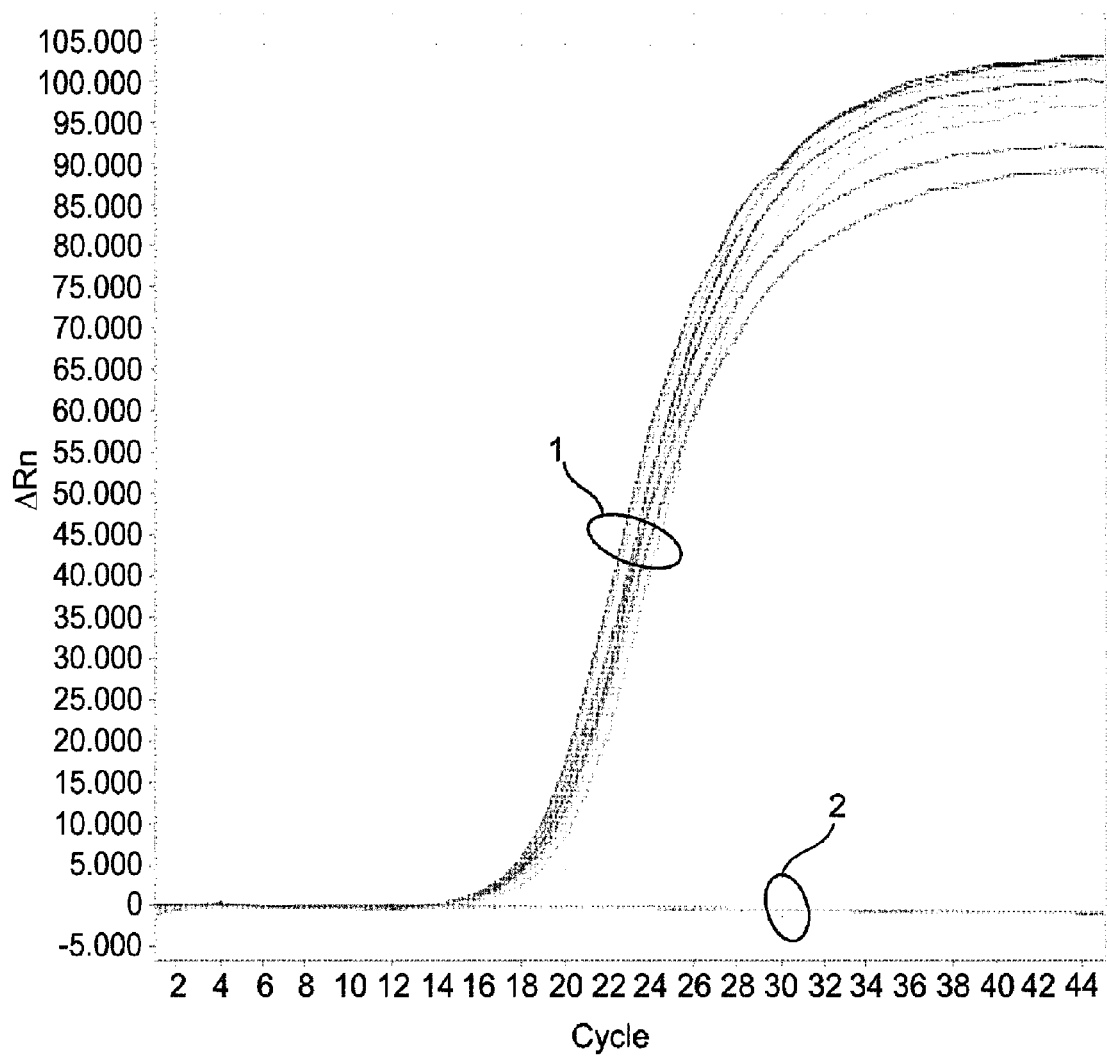
FIG. 3. Data from Split Primers Targeting Dengue virus. Results from combinations of primers in FIG. 2 are shown (combinations include F1 and R1; F1 and R2; F1 and R3; F2 and R1; F2 and R2; and F2 and R3). Each combination of primers was run in a real-time PCR machine in the presence (growth curve, marked by oval 1) and absence (flat line, marked by oval 2) of DNA derived from Dengue virus.

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

As used herein, the singular forms "a", "an", and "the" may refer to plural articles unless specifically stated otherwise. Thus, for example, references to a method of manufacturing, derivatizing, or treating "an analyte" may include a mixture of one or more analytes. Furthermore, the use of grammatical equivalents such as "nucleic acids", "polynucleotides", or "oligonucleotides" are not meant to imply differences among these terms unless specifically indicated.

Embodiments herein generally relate to technology for nucleic acid amplification or extension.

One disadvantage of current nucleic acid amplification technologies is the need for a high degree of primer complementarity with the target sequence. Some targets, like genomes in human immunodeficiency virus (HIV) populations, are highly polymorphic, thus complicating efforts to synthesize a primer exactly complementary to any given strand in an HIV genome by presenting mismatches to a primer intended to amplify a region of the HIV genome in all or multiple HIV viral populations. Such mismatches may prevent primer from annealing to the template, preventing the amplification reaction from taking place, and resulting in false negatives.

One method to overcome this disadvantage involves the design of degenerate primer populations, or primer populations comprised of mixtures of primers differing from one another at one or more bases. However, these degenerate primers decrease the specificity of a reaction and decrease the concentration of desired primers, while simultaneously increasing the risk of "primer dimer" formation and nonspecific amplification.

Another disadvantage of current nucleic acid amplification technologies is the need to find regions of about 50% GC content for primer binding and amplification. Finding a pair of conserved regions can be difficult. This problem is further complicated when these conserved regions are interrupted by GC-rich or AT-rich sequences, or by regions of polymorphic diversity so that the conserved regions with the appropriate GC content are no longer of sufficient length to support primer binding. New primer design methods are needed to overcome these challenges.

Some embodiments herein can overcome one or more of the disadvantages with other technologies.

To facilitate understanding of the disclosure, a number of terms are defined below.

DEFINITIONS

The term "amplicon" refers to a nucleic acid product generated in an amplification reaction.

The term "amplification" refers to the process in which extension of complementary DNA from the primer through the entire amplicon occurs at least once, and preferably more than once, in a cyclic process such that the number of copies of a nucleic acid sequence is increased in either a linear or logarithmic fashion at every cycle.

The term "complementary strand" refers to a nucleic acid sequence strand which, when aligned with the nucleic acid sequence of one strand of the target nucleic acid, such that the 5' end of the sequence is paired with the 3' end of the other sequence in antiparallel association, forms a stable duplex. Complementarity need not be perfect. Stable duplexes can be formed with mismatched nucleotides. This strand may be referred to as the "reverse complement" of the strand with which it forms a stable duplex.

The terms "detect," "detection" or "detecting the presence or absence of an analyte" refer to a process of providing qualitative or quantitative information about an analyte.

The terms "polynucleotide", "oligonucleotide" or "nucleic acid" refer to polydeoxyribonucleotides (DNA), polyribonucleotides (RNA), nucleic acid analogs and derivatives thereof. There is no intended distinction between the length of a "polynucleotide", "oligonucleotide" or "nucleic acid".

The term "primer" refers to an oligonucleotide that functions to initiate a nucleic acid replication, amplification or extension process.

The term "target" refers to an analyte to which a probe is designed to bind or anneal. In some embodiments, the target is the analyte which is being detected.

The term "replication" refers to the process in which a complementary strand of a nucleic acid strand is synthesized by a polymerase enzyme. In a "primer directed" replication, this process generally requires a hydroxyl group (OH) at the 3' end of (deoxy)ribose moiety of the terminal nucleotide of a duplexed "primer" to initiate replication.

The term "reaction temperature" refers to the temperature at which accurate base pairing or hybridization and/or extension occurs or may occur. For example, in some aspects the reaction temperature can be between about 25° C. and 95° C., preferably between about 45° C. and 60° C.

The term "single nucleotide polymorphism" (SNP) refers to a single-base variation in the genetic code of an individual with respect to a reference sequence.

The term "split primer" refers to a primer which is capable of binding with at least two distinct locations on a target nucleic acid which are physically separated by from 1 to 1000 bases, between about 3 and about 200 bases, between about 3 and about 100 bases, or between about 5 and about 50 bases.

The term "variant" or "mutant" analyte refers to an analyte that is different than its wildtype counterpart.

The term "wildtype" refers to the typical form of an organism, strain, gene, or characteristic as it most commonly occurs in nature, as distinguished from mutant forms (e.g., forms that differ from the wild-type).

Analyte

In general, a primer is designed to specifically bind to a particular nucleic acid sequence. When referring to a primer, the phrase "specifically bind(s)" or "bind(s) specifically" refers to a primer that has intermediate or high binding affinity, exclusively or predominately, to a target molecule with a high degree of sequence complementarity to the primer over much or all of the length of the primer. The phrase "specifically bind(s) to" refers to a binding reaction which is predominant with the target in the presence of a heterogeneous population of other biologics. Thus, under designated assay conditions, the specified binding region binds preferentially to a particular target and does not bind in a significant amount to other components present in a test sample. Specific binding to a target under such conditions can involve a binding moiety that is selected for its specificity for a particular target. A variety of assay formats can be used to select binding regions that are specifically reactive with a particular analyte.

Analytes include organisms such as viruses and bacteria or an individual or individuals, and may be found in locations including, but not limited to, skin, plasma, serum, spinal fluid, lymph fluid, synovial fluid, urine, tears, blood cells, organs, or tumors, and also samples of in vitro cell culture constituents, such as conditioned medium resulting from the growth of cells in cell culture medium, recombinant cells or cell components. Analytes can also be from environmental samples such as air or water samples, or may be from forensic samples from biological or non-biological sources, including clothing, tools, publications, letters, furniture, etc. Additionally, analytes can also come from synthetic sources. The analytes in the embodiments described herein can be provided in a sample that can be a crude sample, a partially purified or substantially purified sample, or a treated sample, where the sample can contain, for example, other natural components of biological samples, such as proteins, lipids, salts, nucleic acids, or carbohydrates.

A variety of modified and nonmodified nucleic acid bases can be used in the embodiments described herein. Examples include peptide nucleic acids, locked nucleic acids, 2'-halide ribose substitutions and numerous others known to one of ordinary skill in the art.

Each oligonucleotide primer in accordance with the embodiments described herein can vary from about five nucleotides in length to over about 1,000 nucleotides in length. Preferably the primers are between 5 and 200 nucleotides in length and more preferably between 10 and 50 nucleotides in length or any subrange or individual value there between.

In some embodiments, the primers are designed for maximum specificity. The melting temperature of the primer is preferably designed at between about 7° C. and about 10° C. over the reaction temperature. For assays that operate based on base-pairing between nucleotides, primer lengths to achieve these melting temperatures preferably range between about 5 and about 25 bases, more preferably between about 10 and about 25 bases, and even more preferably between about 15 and about 25 bases.

In some embodiments, large affinities are desired for maximum sensitivity or to allow binding of variants. Melting temperatures for the primer are preferably designed to be between about 10° C. to about 50° C. over the reaction temperature.

For embodiments targeting nucleic acids, primer lengths range preferably between about 20 and about 70 nucleotides, more preferably between about 25 and about 50 nucleotides, and most preferably between about 25 and about 40 nucleotides.

The melting temperature can be determined similarly to normal nearest neighbor thermodynamics calculations in primer design. In some of the embodiments described herein, the primer binds to two or more distinct regions on a target. In order to approximate melting temperature, nearest neighbor calculators such as Mfold can be employed. (M. Zuker, *Nucleic Acids Res* 31(13), 3406-15 (2003); D. H. Mathews et al., *J Mol Biol* 288, 911-40 (1999), which is incorporated herein by reference in its entirety). For example, both the primer and the target sequence can be entered into the Mfold software to calculate the melting temperature. One difference is that the nearest neighbor predictions revealing the lowest energy form should reveal one or more loops, depending on the number of binding sites of the primer that hybridized to the target sequence (e.g., two or three sites, as shown in FIG. 1).

The determination of the number of primer binding sites depends on the needs of the assay for which the primer is being designed. In a preferred embodiment, less than four binding sites are used, and more preferably, less than three binding sites are used.

In preferred embodiments, the determination of the location for the primer binding sites can be made based on the degree of sequence conservation, uniqueness from other targets, optimal GC content, the presence of little to no secondary structure, lack of self-complementarity, or other factors known to one of ordinary skill in the art.

One preferred consideration in designing a split primer can be the ratio of the lengths of the different binding regions. In a preferred embodiment, the 3' binding region of the primer should exhibit equal or greater affinity to a target compared to any of the other binding regions. The affinity can be determined by nearest neighbor thermodynamic calculations or can be assessed qualitatively through assessment of the length of the binding regions and the GC content of each. In general, regions of equal length and similar GC content will have similar affinities. Regions that are longer or have greater GC content will generally have higher affinities, while regions that are shorter or have lower GC content will generally have lower affinities. Regions that are longer with lower GC content or shorter with high GC content can be assessed using nearest neighbor calculations.

The 3' binding region of the primer preferably has equal or higher affinity to a target compared to any other region to insure that the 3' binding region has a maximum probability of being bound in order to initiate primer extension. If the 3' end is not hybridized to the target, then it cannot prime synthesis of DNA off of the 3' hydroxyl group, lowering the efficiency of the amplification or extension process. If the 3' binding region has relatively low affinity compared to the other primer binding regions, then it will be hybridized to the target only a fraction of the time compared to the other primer binding regions. The lower the affinity compared to the other binding regions, the lower the probability that it will be hybridized to the target at any point in time. Thus, in preferred embodiments, primer extension efficiency is maximized and the 3' binding region is designed to have relatively high or equal affinity compared to the other binding regions.

Another factor that can be considered is the distance between binding regions on the target. In some embodiments, the distance can be, for example, less than about 1,000 bases. Preferably, the distance can be, for example, less than about 100 bases, and even more preferably, less than about 50 bases. The distance between the binding sites will affect the affinity of the primer for the target. Typically, larger distances will reduce the affinity of the primer for the target, while shorter distances will increase the affinity of the primer for the target.

If the distance between binding sites is unalterable due to non-ideal content between the binding regions, then the affinity can be adjusted by increasing or decreasing the length of the primer binding regions. The exact balance of distance between binding sites and the strength of the individual binding sites (e.g., as determined by length and/or GC content) can be evaluated using nearest neighbor principles, such as those employed by Mfold.

The decision to utilize a split primer can be prompted in some embodiments by the need to find unique, conserved locations. In some embodiments, a highly conserved region across several species may be identified in which a single base is not conserved. In an effort to utilize a single primer (e.g., as opposed to degenerate primers), a split primer can be employed, skipping the single variable base and thereby allowing the targeting of each species with a primer that has equal affinity for all targeted species.

In some embodiments, an organism from a highly polymorphic population may have few regions of conservation relative to the population as a whole, none of which are long enough for a primer. However, by designing a split primer which targets two or more of these short, conserved regions, the primer obtains sufficient affinity to be used in the reaction.

In some embodiments, several conserved regions of a target are of sufficient length to design a primer, but the content is poor due to excessive secondary structure, non-optimal GC content, overlap with other organisms, or other reasons known to one of ordinary skill in the art. By using a split primer, two or more short regions possessing preferred qualities for primer design may be targeted with sufficient affinity for amplification or extension to occur.

The examples provided herein give those of ordinary skill in the art a disclosure and description of how to make and use some of the preferred embodiments, and are not intended to limit the scope of what the inventors regard as their invention. Modifications of the above-described modes for carrying out the some aspects of the technology that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

EXAMPLES

Example 1

Split Primers

Examples of the split primers described herein are shown in FIG. 1.

Example 2

Dengue Virus Split Primers

Dengue virus has four genetically divergent subtypes or serotypes. A small conserved region exists in the four subtypes at the 3' end of the virus. However, this region only has a few short sequences that are fully conserved. Split primers were used to target the 5' end of the primer to one conserved region and the 3' end of the primer to another conserved region of the Dengue virus. The sequences of these split primers are shown in FIG. 2, along with surrounding regions of the virus. FIG. 2 demonstrates that the primers are located in regions of highly conserved sequence.

Example 3

Real-Time PCR with Dengue Virus Split Primers

Master mixes were made with 250 nM of the combination of forward (F1 and F2) and reverse primers (R1, R2, and R3) with SYBR® Green Master Mix (Invitrogen, Carlsbad, Calif.). 5 μL of Master Mix was added to 5 μL of samples positive or negative for Dengue virus nucleic acid sequences. The PCR was cycled using the following protocol: 55° C. for 10 minutes, 95° C. for 20 seconds, followed by 45 cycles of 95° C. for 1 second and 55° C. for 20 seconds. Each of the combinations had 100% accuracy with no false positives or false negatives (FIG. 3).

What is claimed is:

1. A method of assaying for a nucleic acid sequence, the method comprising contacting a split primer with a sample that may comprise DNA derived from a Dengue virus under conditions necessary for the amplification, wherein the split primer has two regions comprising a first sequence complementary to a first region of a target nucleic acid sequence and a second sequence complementary to a second region of a target nucleic acid, and wherein the two regions of the split primer are not separated by an intervening base, and wherein the split primer targets two or more unique locations on a target nucleic acid from the Dengue virus, and wherein the two or more unique locations are separated by at least one nucleic acid base, and wherein amplification of the target sequence is carried out in the presence of a polymerase and a reverse primer under conditions necessary for amplification or extension, and is indicative of the presence of DNA derived from Dengue virus in the sample.

2. The method of claim 1, wherein the two or more unique locations are separated by, at least three nucleic acid bases.

3. The method of claim 1, wherein the two or more unique locations are separated by at least five nucleic acid bases.

4. The method of claim 1, further comprising detecting a product from the amplification.

5. The method of claim 1, further comprising detecting the presence of the target nucleic acid.

6. A method of amplifying a target nucleic acid sequence, comprising:

providing a split primer, wherein the split primer has two regions comprising a first sequence complementary to a first region of a target nucleic acid sequence and a second sequence complementary to a second region of a target nucleic acid, wherein the two regions of the split primer are not separated by an intervening base, and wherein the first and second regions of the target nucleic acid sequence are separated by at least one nucleic acid base;

hybridizing the split primer to the first and second regions of the target nucleic acid sequence in the presence of a polymerase and a reverse primer under conditions necessary for amplification; and amplifying the target nucleic acid sequence.

* * * * *

UNITED STATES PATENT AND TRADEMARK OFFICE
CERTIFICATE OF CORRECTION

| | | |
|---|---|---|
| PATENT NO. | : 8,673,569 B2 | Page 1 of 1 |
| APPLICATION NO. | : 12/830242 | |
| DATED | : March 18, 2014 | |
| INVENTOR(S) | : Brent C. Satterfield | |

It is certified that error appears in the above-identified patent and that said Letters Patent is hereby corrected as shown below:

Title Page

Item (73) Correct Name of Assignee: should be -- Co-Diagnostics, Inc., Sandy, Utah --.

Signed and Sealed this
Sixteenth Day of September, 2014

Michelle K. Lee
*Deputy Director of the United States Patent and Trademark Office*